(12) United States Patent
Boernert et al.

(10) Patent No.: US 10,345,407 B2
(45) Date of Patent: Jul. 9, 2019

(54) MR FINGERPRINTING FOR DETERMINING PERFORMANCE DEGRADATION OF THE MR SYSTEM

(71) Applicant: KONINKLIJKE PHILIPS N.V., Eindhoven (NL)

(72) Inventors: Peter Boernert, Eindhoven (NL); Mariya Ivanova Doneva, Eindhoven (NL); Thomas Erik Amthor, Eindhoven (NL); Peter Koken, Eindhoven (NL); Jochen Keupp, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 160 days.

(21) Appl. No.: 15/547,622

(22) PCT Filed: Jan. 22, 2016

(86) PCT No.: PCT/EP2016/051274
§ 371 (c)(1),
(2) Date: Jul. 31, 2017

(87) PCT Pub. No.: WO2016/124414
PCT Pub. Date: Aug. 11, 2016

(65) Prior Publication Data
US 2018/0031653 A1   Feb. 1, 2018

(30) Foreign Application Priority Data
Feb. 2, 2015   (EP) ..................................... 15153472

(51) Int. Cl.
*G01R 33/46*   (2006.01)
*G01R 33/54*   (2006.01)
(Continued)

(52) U.S. Cl.
CPC ......... *G01R 33/4625* (2013.01); *G01R 33/54* (2013.01); *G01R 33/546* (2013.01);
(Continued)

(58) Field of Classification Search
CPC .. G01R 33/4625; G01R 33/546; G01R 33/58; G01R 33/54; G01R 33/4828; G06F 19/00
See application file for complete search history.

(56) References Cited

U.S. PATENT DOCUMENTS 6,115,489 A * 9/2000 Gupta ................... G06F 19/321
   382/141
6,609,217 B1   8/2003 Bonissone
(Continued)

OTHER PUBLICATIONS

Ma et al "Magnetic Resonance Fingerprinting" Nature vol. 495, pp. 187-193 Mar. 2013.
(Continued)

*Primary Examiner* — Tung X Nguyen
*Assistant Examiner* — Dominic E Hawkins

(57) ABSTRACT

The invention provides for a method of operating a magnetic resonance system for acquiring magnetic resonance data (152) from a phantom (124) within a measurement (zone 108). The phantom comprises a known volume of at least one predetermined substance ((128), 130). The method comprises the step of acquiring (300) the magnetic resonance data by controlling the magnetic resonance system with pulse sequence instructions (150). The pulse sequence instructions cause the magnetic resonance system to acquire the magnetic resonance data according to a magnetic resonance fingerprinting technique. The pulse sequence instructions specify a train of pulse sequence repetitions. Each pulse sequence repetition has a repetition time chosen from a distribution of repetition times. Each pulse sequence repetition comprises a radio frequency pulse chosen from a distribution of radio frequency pulses. The distribution of
(Continued)

radio frequency pulses cause magnetic spins to rotate to a distribution of flip angles. Each pulse sequence repetition comprises a sampling event where the magnetic resonance signal is sampled for a predetermined duration at a sampling time before the end of the pulse sequence repetition. The method further comprises determining (302) one or more performance degradation conditions of the magnetic resonance system by comparing the magnetic resonance data with a magnetic resonance fingerprinting dictionary (154). The magnetic resonance fingerprinting dictionary contains a listing of magnetic resonance signals for a set of system states in response to execution of the pulse sequence instructions for each of the at least one predetermined substance.

14 Claims, 6 Drawing Sheets

(51) Int. Cl.
    *G01R 33/58* (2006.01)
    *G16H 40/40* (2018.01)
    *G01R 33/48* (2006.01)
(52) U.S. Cl.
    CPC ............ *G01R 33/58* (2013.01); *G16H 40/40* (2018.01); *G01R 33/4828* (2013.01)
(56) References Cited

U.S. PATENT DOCUMENTS

| | | | | |
|---|---|---|---|---|
| 6,680,995 | B2* | 1/2004 | Toth | G06K 9/033 378/4 |
| 2009/0302845 | A1* | 12/2009 | Biber | G01R 33/3415 324/318 |
| 2012/0235678 | A1 | 9/2012 | Seiberlich et al. | |
| 2013/0265047 | A1 | 10/2013 | Griwold et al. | |
| 2013/0271132 | A1 | 10/2013 | Griswold | |
| 2014/0037171 | A1* | 2/2014 | Bhat | G06T 11/003 382/131 |
| 2014/0167752 | A1* | 6/2014 | Hanada | A61B 5/055 324/307 |
| 2014/0167754 | A1* | 6/2014 | Jerecic | G01R 33/561 324/309 |
| 2015/0186606 | A1* | 7/2015 | Kuang | A61B 5/055 702/19 |
| 2015/0302579 | A1* | 10/2015 | Griswold | G01R 33/5608 382/128 |
| 2016/0282430 | A1* | 9/2016 | Gulani | G01R 33/4828 |

OTHER PUBLICATIONS

Cao et al "Bloch-Based MRI System Simulator Considering Realistic Electromagnetic Fields for Calculation of Signal, Noise and Specific Absorption Rate" Magnetic Res in Med, 72: p. 237-247 (2014).

Cao "Advances in Simulation and Thermography for High Field MRI" Dissertation Pennsylvania State University (Aug. 2013).

Sarracanie et al "High Speed MR Fingerprinting at 6.5 MT" ISMRM Joint Annual Meeing Conference Paper 2014.

Jiang et al "MR Fingerprinting Using Spiral Quest", Proc. Intl. Soc. Mag.Reson. Med 21 (2013) p. 19.

* cited by examiner

MR FINGERPRINTING FOR DETERMINING PERFORMANCE DEGRADATION OF THE MR SYSTEM

CROSS REFERENCE TO RELATED APPLICATIONS

This application is a U.S. national phase application of International Application No. PCT/EP2016/051274, filed on Jan. 22, 2016, which claims the benefit of EP Application Serial No. 15153472.4 filed on Feb. 2, 2015 and is incorporated herein by reference.

TECHNICAL FIELD OF THE INVENTION

The invention relates to magnetic resonance imaging, in particular to the diagnosis of performance degradation and/or faults in the magnetic resonance imaging apparatus.

BACKGROUND OF THE INVENTION

Magnetic Resonance (MR) fingerprinting is a new technique where a number of RF pulses, distributed in time, are applied such that they cause signals from different materials or tissues to have a unique contribution to the measured MR signal. A limited dictionary of precalculated signal contributions from a set or fixed number of substances is compared to the measured MR signals and within a single voxel the composition can be determined. For example if it is known that a voxel only contains water, fat, and muscle tissue the contribution from these three materials need only be considered and only a few RF pulses are needed to accurately determine the composition of the voxel.

The magnetic resonance fingerprinting technique was introduced in the journal article Ma et al., "Magnetic Resonance Fingerprinting," Nature, Vol. 495, pp. 187 to 193, doi:10.1038/nature11971. The magnetic fingerprinting technique is also described in United States patent applications US 2013/0271132 A1 and US 2013/0265047 A1.

SUMMARY OF THE INVENTION

The invention provides for a method of operating a magnetic resonance imaging system, a magnetic resonance imaging system and a computer program product in the independent claims. Embodiments are given in the dependent claims.

The Nature article by Ma et al. introduces the basic idea of magnetic resonance fingerprinting and terminology which is used to describe this technique such as the dictionary. Herein the idea of a magnetic resonance fingerprinting dictionary is used similarly, however the magnetic resonance fingerprinting is carried out on a known phantom. Instead of identifying substances within a volume or voxel using the magnetic resonance fingerprinting dictionary, the state of various components of the magnetic resonance imaging system or apparatus is deduced. The magnetic resonance fingerprinting dictionary as used herein encompasses a magnetic resonance fingerprinting dictionary for measurements performed on a known phantom and with variations in various magnetic resonance imaging system performance states and/or failure modes.

The entries in the dictionary are constructed by modeling of changes in the performance of various components of the magnetic resonance imaging system. For example if the RF transmitter in a magnetic resonance imaging system is functioning perfectly then one would expect a different measured magnetic resonance signals than if the RF transmitter is beginning to experience performance depredation or close to failure. Similar variations in the performance of other components such as the gradient power supply, the state of the gradient coils, the receive coils, the transmit coils or antennas, the magnet system, operation of the patient table, and/or the physiology system.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further understood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic/nuclear spins using the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

In one aspect the invention provides for a method of operating a magnetic resonance system for acquiring magnetic resonance data from a phantom within a measurement zone. The phantom comprises a known volume of at least one predetermined substance. The predetermined substances may comprise a material which is able to be detected using magnetic resonance imaging or other nuclear magnetic resonance protocols. The magnetic resonance system comprises a memory for storing pulse sequence instructions. The pulse sequence instructions cause the magnetic resonance system to acquire the magnetic resonance data according to a magnetic resonance fingerprinting technique.

The pulse sequence instructions specify a train of pulse sequence repetitions. Each pulse sequence repetition has a repetition time chosen from a distribution of repetition times. Each pulse sequence repetition comprises a radio-frequency pulse chosen from a distribution of radio-frequency pulses. The distribution of radio-frequency pulses causes magnetic spins to rotate to a distribution of flip angles. In addition to the distribution of repetition times other parameters such as the flip angle, the gradients and other parameters may also be varied. The distribution of radio-frequency pulses causes magnetic spins to rotate to a distribution of flip angles. Each pulse sequence repetition comprises a sampling event where the magnetic resonance signal is sampled for a predetermined duration at a sampling time before the end of the pulse sequence repetition. The sampling time is chosen from a distribution of sampling times. The magnetic resonance data is acquired during the sampling event.

The method comprises the step of acquiring the magnetic resonance data by controlling the magnetic resonance system with the pulse sequence instructions. The method further comprises the step of determining one or more performance degradation conditions. This may be done by comparing the magnetic resonance data with a magnetic resonance fingerprinting dictionary. The performance degradation conditions are descriptive of the magnetic resonance imaging system or the performance of various components. The magnetic resonance fingerprinting dictionary contains a listing of magnetic resonance signals for a set of system states in response to execution of the pulse sequence instructions for each of the at least one predetermined substance. The system states can be described as a combination of system parameters that influence the signal evolution. The set of system states represents faults, malfunctions or performance degradation conditions by different components of the magnetic resonance imaging system. For example the antennas used or performance of various radio-frequency components may have degraded performance as time goes on. These may be difficult to diagnose or to determine what component is causing the performance of the magnetic resonance system to decline. The method of the invention employs MR fingerprinting techniques to determine if any of a performance degradation condition occurs, a fault or malfunction occurs, whether in isolation or in combination. Moreover, if the occurrence of a performance degradation condition, a fault or a malfunction is determined, then on the basis of the MR fingerprinting technique by way of comparison to the MR fingerprinting dictionary, also the details of the determined performance degradation, fault or malfunction may be established.

This method may be beneficial because it uses the known magnetic resonance fingerprinting technique to diagnose failures and/or marginal components in a magnetic resonance system. To do this a phantom with a known composition or structure is used. The magnetic resonance signal can be modeled for various conditions of the magnetic resonance system. For instance if the radio-frequency amplifier or transceiver is not performing to spec the recorded signal can be modeled with the reduced capacity of this device to generate appropriate entries in the magnetic resonance fingerprinting dictionary to identify those potential circumstances. Examples may enable accurate determination of one or more faults or failures of the system.

In another embodiment the pulse sequence instructions comprise multiple segments. In this case the pulse sequence instructions are broken into multiple portions that may be executed independently. The magnetic resonance fingerprinting dictionary is arranged as a decision tree for determining the one or more faults or borderline cases that comprise each of the multiple segments. The decision tree has multiple entries. Each of the multiple entries is connected by branches. For example when one of the entries is reached there may be a portion of the pulse sequence instructions which are executed.

The resulting signal may then be compared to a magnetic resonance signal which corresponds to the properties/system performance states of each of the branches. Pattern matching or another algorithm which may compare the measured signal to the calculated signals in the dictionaries associated with each of the branches. This may then be used to decide which branch of the decision tree to follow. After a branch is followed another entry is chosen. This entry may have associated with it another segment of the pulse sequence instructions. This is then executed and the decision tree is followed until the fault or faults are diagnosed.

The multiple segments of the pulse sequence instructions comprise a first segment. The multiple entries of the decision tree comprise a first entry which corresponds to the first segment. The method further comprises the step of controlling the magnetic resonance system with the first segment to acquire a first portion of the magnetic resonance data. The method further comprises the step of comparing the first portion of the magnetic resonance data to the first entry in the decision tree to choose a branch which identifies a subsequent segment of the pulse sequence data. Within the decision tree there are "local" decision tree dictionaries that are constructed so that the decision tree is properly traversed.

The method further comprises the step of traversing the decision tree to identify the one or more faults or off-spec situations by repeatedly controlling the magnetic resonance system with the subsequent segment and re-identifying the subsequent segment using the branches of the decision tree. This method may have the benefit of not needing to repeat the entire pulse sequence instructions but only segments which bring the rapid diagnosis of problems with the magnetic resonance system.

In another embodiment the one or more faults are two or more faults or off-spec situations, and are identified as a linear combination of the set of system states. In this technique the techniques which are typically used for performing magnetic resonance fingerprinting are used directly to identify the faults or the probability that a fault occurs with the magnetic resonance system. Ideally one would prefer to have a dictionary entry for every possible fault or combination of faults. This may not always be possible. Combining the faults using a linear or other combination may enable the identification of combination of faults that are not in the dictionary.

In another embodiment the magnetic resonance system is a magnetic resonance imaging system. The measurement zone is an imaging zone. The magnetic resonance system further comprises a magnet for generating a main magnetic field within the measurement zone. The magnetic resonance system further comprises a magnetic field gradient system for generating a gradient magnetic field within the measurement zone to spatially encode the magnetic resonance data. The pulse sequence instructions further comprise instructions to control the magnetic field gradient system to perform spatial encoding of the magnetic resonance data during acquisition of the magnetic resonance data. The spatial encoding divides the magnetic resonance data into discreet voxels.

Execution of the machine-executable instructions further cause the processor to calculate the magnetic resonance fingerprinting dictionary by modeling each of the predetermined substances as one or more spins with the Bloch equations for each of the discreet voxels and for each of the set of system states.

In another embodiment the at least one predetermined substance is two or more substances. The phantom comprises a separate compartment for each of the two or more substances and for different combinations of the set of system states. Having multiple substances may be useful because the magnetic resonance signal from the different substances may be distinct. This may provide separate datasets which can be used separately and this may enable better identification of faults or system degradation of the magnetic resonance system. For example one portion may contain water, a fat or oily tissue phantom, or may contain an aqueous solution with various contrast agents. A magnetic resonance fingerprinting dictionary may be created for each substance and the identification of the faults or off-spec performance may be performed for each one of the substances. This may enable the comparison of the results for each of the two or more substances. This may add greater confidence to a result that is obtained.

In another embodiment the magnetic resonance system is a NMR or nuclear magnetic resonance spectrometer. Execution of the machine-executable instructions further cause the processor to calculate the magnetic resonance fingerprinting dictionary by modeling each of the predetermined substances with the block equations for each of the discreet voxels and for each of the set of system states.

In another embodiment the magnetic resonance system is an NMR spectrometer.

In another embodiment the magnetic resonance system is a magnetic resonance imaging system.

In another embodiment the phantom comprises a temperature control system that further comprises maintaining the phantom temperature within a predetermined temperature range during acquisition of the magnetic resonance data. For example an electric heating system or a heating system which provides a fluid has a temperature within a temperature band may be used to control the temperature of the phantom. In other examples air or other gas may be at a control temperature and then blown through a heat exchange system within the phantom.

In another embodiment the magnetic resonance system comprises a phantom mount for mounting the phantom in a predefined location in the measurement zone. The method further comprises placing the phantom into the phantom mount before acquiring the magnetic resonance data. For example the phantom mount may be a mounting apparatus which mounts to a subject support in a predefined location. This may assist in having reproducible results when making measurements on the phantom. This may enable more accurate determination of pulse or system degradation within the magnetic resonance system.

In another embodiment each pulse sequence repetition comprises at least one gradient pulse chosen from a distribution of gradient pulses. This may be useful in diagnosing failures of the gradient coils and/or the gradient coil power supply.

In another embodiment the method further comprises providing maintenance instructions by comparing the one or more performance degradation conditions to a repair database. For example the repair database may be an electronic or other system which provides detailed repair instructions for a particular degradation condition which is diagnosed.

In another embodiment the method further comprises performing the maintenance instructions to repair the magnetic resonance imaging system. This for instance may be performed by a maintenance or service individual.

In another aspect the invention provides for a magnetic resonance system for acquiring magnetic resonance data from a phantom within a measurement zone. The phantom comprises a known volume of at least one predetermined substance. The magnetic resonance system comprises a memory for storing pulse sequence instructions and machine-executable instructions. The pulse sequence instructions cause the magnetic resonance system to acquire the magnetic resonance data according to a magnetic resonance fingerprinting technique.

The pulse sequence instructions specify a train of pulse sequence repetitions. Each pulse sequence repetition has a repetition time chosen from a distribution of repetition times. Each pulse sequence repetition comprises a radio-frequency pulse chosen from a distribution of radio-frequency pulses. The distribution of radio-frequency pulses causes magnetic spins to rotate to a distribution of flip angles. Each pulse sequence repetition comprises a sampling event where the magnetic resonance signal is sampled for a predetermined duration at a sampling time before the end of the pulse sequence repetition. The sampling time is chosen from a distribution of sampling times. The magnetic resonance data is acquired during the sampling event. The magnetic resonance system further comprises a processor for controlling the magnetic resonance system. Execution of the machine-executable instructions causes the processor to acquire the magnetic resonance data by controlling the magnetic resonance system with the pulse sequence instructions.

Execution of the machine-executable instructions further cause the processor to determine one or more performance degradation conditions of the magnetic resonance system by comparing the magnetic resonance data with the magnetic resonance fingerprinting dictionary. The magnetic resonance fingerprinting dictionary contains a listing of magnetic resonance signals for a set of system states in response to execution of the pulse sequence instructions for each of the at least one predetermined substances. The set of system states represents faults, malfunctions or performance degradation conditions by different components of the magnetic resonance imaging system. The performance degradation conditions or faults may correspond to certain deviations in system parameter that result in unique magnetic resonance signals or a set of signals and can therefore be detected.

In another aspect the invention provides for a computer program product comprising machine-executable instructions for execution by a processor controlling the magnetic resonance system for acquiring magnetic resonance data from a phantom within a measurement zone. The phantom comprises a known volume of at least one predetermined substance. The magnetic resonance system comprises a memory for storing pulse sequence instructions. The pulse sequence instructions cause the magnetic resonance system to acquire the magnetic resonance data according to a magnetic resonance fingerprinting technique.

The pulse sequence instructions specify a train of pulse sequence repetitions. Each pulse sequence repetition has a repetition time chosen from a distribution of repetition times. Each pulse sequence repetition comprises a radio-frequency pulse chosen from a distribution of radio-frequency pulses. The distribution of radio-frequency pulses causes magnetic spins to rotate to a distribution of flip angles. Each pulse sequence repetition comprises a sampling event where the magnetic resonance signal is sampled for a predetermined duration at a sampling time before the end of the pulse sequence repetition. The sampling time is chosen from a distribution of sampling times. The magnetic resonance data is acquired during the sampling event. Execution of the machine-executable instructions causes the processor to acquire the magnetic resonance data by controlling the magnetic resonance system with pulse sequence instructions.

Execution of the machine-executable instructions further cause the processor to determine one or more performance degradation conditions of the magnetic resonance imaging system by comparing the magnetic resonance data with a magnetic resonance fingerprinting dictionary. The magnetic resonance fingerprinting dictionary contains a listing of magnetic resonance signals for a set of system states in response to execution of the pulse sequence instructions for each of the at least one predetermined substance. The set of system states represents possible faults, possible malfunctions, or possible performance degradation conditions by different components of the magnetic resonance imaging system.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
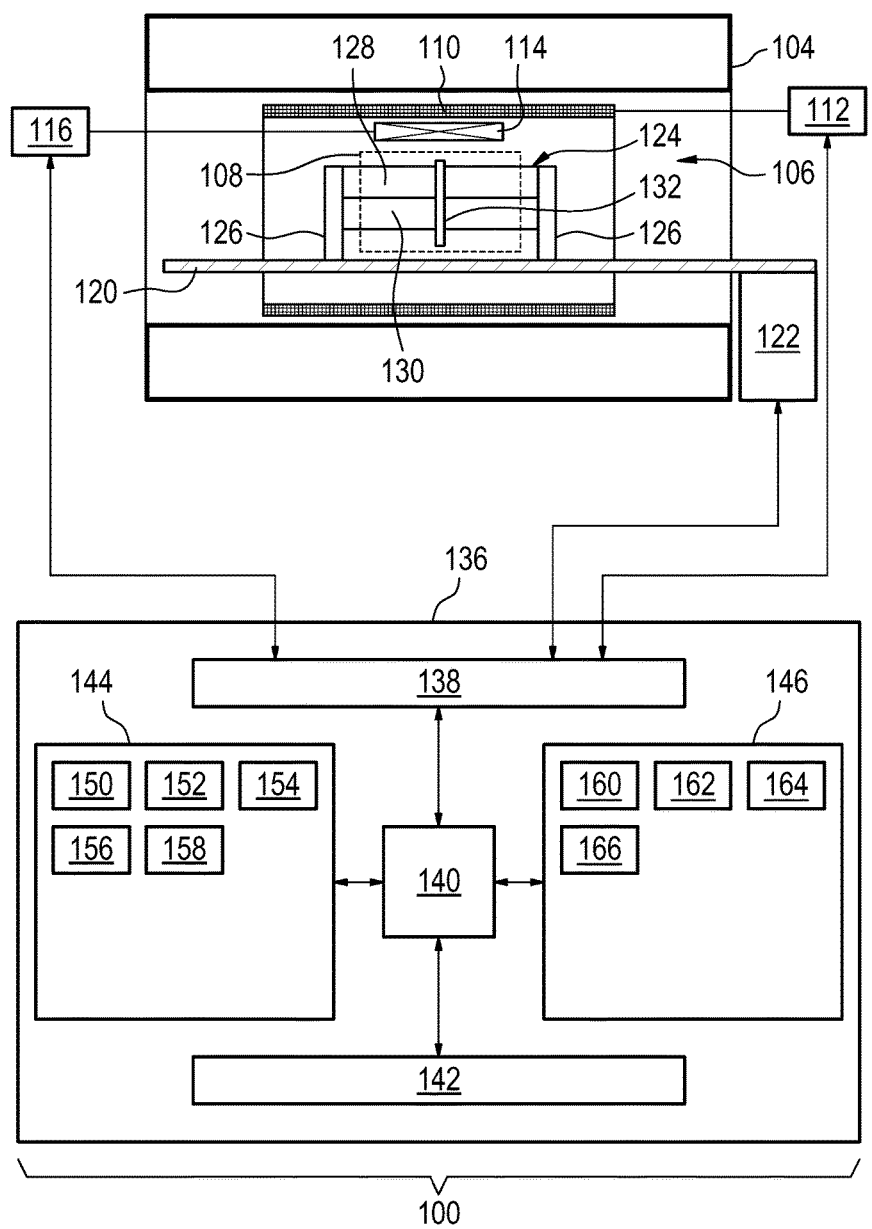
FIG. 1 illustrates an example of a magnetic resonance imaging system.

FIG. 1 shows an example of a magnetic resonance imaging system 100 with a magnet 104. The magnet 104 is a superconducting cylindrical type magnet 104 with a bore 106 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 106 of the cylindrical magnet 104 there is an imaging zone 108 where the magnetic field is strong and uniform enough to perform magnetic resonance imaging.

Within the bore 106 of the magnet there is also a set of magnetic field gradient coils 110 which is used for acquisition of magnetic resonance data to spatially encode magnetic spins within the imaging zone 108 of the magnet 104. The magnetic field gradient coils 110 connected to a magnetic field gradient coil power supply 112. The magnetic field gradient coils 110 are intended to be representative. Typically magnetic field gradient coils 110 contain three separate sets of coils for spatially encoding in three orthogonal spatial directions. A magnetic field gradient power supply supplies current to the magnetic field gradient coils. The current supplied to the magnetic field gradient coils 110 is controlled as a function of time and may be ramped or pulsed.

Adjacent to the imaging zone 108 is a radio-frequency coil 114 for manipulating the orientations of magnetic spins within the imaging zone 108 and for receiving radio transmissions from spins also within the imaging zone 108. The radio frequency antenna may contain multiple coil elements. The radio frequency antenna may also be referred to as a channel or antenna. The radio-frequency coil 114 is connected to a radio frequency transceiver 116. The radio-frequency coil 114 and radio frequency transceiver 116 may be replaced by separate transmit and receive coils and a separate transmitter and receiver. It is understood that the radio-frequency coil 114 and the radio frequency transceiver 116 are representative. The radio-frequency coil 114 is intended to also represent a dedicated transmit antenna and a dedicated receive antenna. Likewise the transceiver 116 may also represent a separate transmitter and receivers. The radio-frequency coil 114 may also have multiple receive/transmit elements and the radio frequency transceiver 116 may have multiple receive/transmit channels, those are linked for the transmit path to individual amplifiers not shown in Fia and for the receive part to appropriate preamplifiers and the corresponding digitalization technology, comprising all individual components with a certain risk to fail.

The subject support 120 is attached to an optional actuator 122 that is able to move the subject support and a subject or a phantom 124 through the imaging zone 108. Within the bore of the magnet 106 there is a phantom 124 attached to the subject support 120 by two phantom mounts 126. These for instance may lock into the subject support 120 and provide a defined geometry or position of the phantom 124 relative to the magnet 104. In this example the phantom 124 has a first compartment 128 filled with a first substance and a second compartment filled with a second substance 130. This is intended to be exemplary. There for instance may only be one compartment or there may be more than two compartments. When there are more than one compartment a slice 132 may be positioned so that data can be received from both compartments 128, 130.

The transceiver 116, the magnetic field gradient coil power supply 112 and the actuator 122 are all see as being connected to a hardware interface 138 of computer system 136. The computer storage 144 is shown as containing pulse sequence instructions 150 for performing a magnetic resonance fingerprinting technique. The computer system 136 further comprises a processor 140. The processor 140 is connected to the hardware interface 138. The hardware interface 138 enables the processor 140 to send and receive data and commands to the magnetic resonance imaging system 100. The computer system 136 further comprises a user interface 142, computer storage 144 and computer memory 146 that are in communication with the processor 140.

The contents of the computer storage 144 and the computer memory 146 may be interchangeable. For example, the contents or partial contents of the computer storage 144 may be duplicated in the computer memory 146 and vice versa.

The pulse sequence instructions 150 specifies a train of pulse sequence repetitions. Each pulse sequence repetition has a repetition time chosen from a distribution of repetition times. Each pulse sequence repetition comprises a radio frequency pulse chosen from a distribution of radio frequency pulses. The distribution of radio frequency pulses cause magnetic spins to rotate to a distribution of flip angles. Each pulse sequence repetition comprises a sampling event where the magnetic resonance signal is sampled for a predetermined duration at a sampling time before the end of the pulse sequence repetition. The sampling time is chosen from a distribution of sampling times. The magnetic resonance data is acquired during the sampling event.

The computer storage 144 is further shown as containing magnetic resonance data 152 that was acquired using the pulse sequence instructions 150 to control the magnetic resonance imaging system 100. The computer storage 144 is further shown as containing a magnetic resonance fingerprinting dictionary 154. The computer storage is further shown as containing a magnetic resonance image 156 that was reconstructed using the magnetic resonance data 152 and the magnetic resonance fingerprinting dictionary 154.

The computer memory 146 contains a control module 160 which contains such code as operating system or other instructions which enables the processor 140 to control the operation and function of the magnetic resonance imaging system 100.

The computer memory 146 is further shown as containing a magnetic resonance fingerprint dictionary generating module 162. The fingerprint generating module 162 may model one or more spins using the Bloch equation for each voxel and various states of the magnetic resonance imaging system apparatus to construct the magnetic resonance fingerprinting dictionary 154. The computer memory 146 is further shown as containing an image reconstruction module that uses the magnetic resonance data 152 and the magnetic resonance fingerprinting dictionary 154 to reconstruct the magnetic resonance image 156. For example the magnetic resonance image 156 may be a rendering of the spatial distribution of one or more of the predetermined substances within the subject phantom 124.

The computer storage 144 is further shown as containing an identified performance degradation condition 158 that was identified using the magnetic resonance data 152 and the magnetic resonance fingerprinting dictionary 154.

The computer memory 146 is further shown as containing a repair database 166 that provides repair instructions for identified performance degradation conditions 158. For example once a performance degradation condition is identified this may be used to look up repair instructions which are retrieved from the repair database 166. These for instance may be displayed or printed and provided to a service individual for maintenance or repair of the magnetic resonance imaging system 100.

The contents of the computer storage 144 and the computer memory 146 may be partially or entirely duplicated by each other. Contents shown in the computer storage 144 may be instead in the computer memory 146 and vice versa.

The example of FIG. 1 could be modified so that the magnetic resonance imaging system or apparatus 100 is equivalent to a Nuclear Magnetic Resonance (NMR) spectrometer. Without gradient coils 110 and the gradient coil power supply 112 the apparatus 100 would perform a 0-dimensional measurement in the imaging zone 108.

Figure 2:
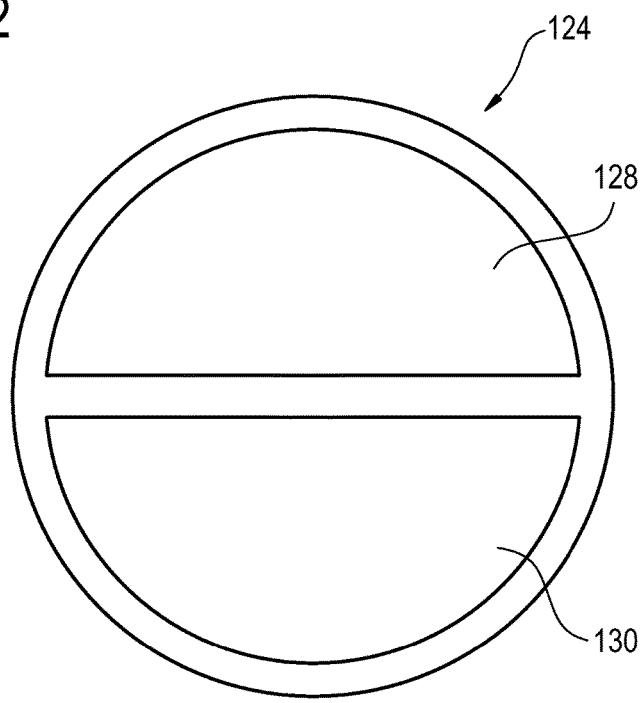
FIG. 2 illustrates a cross section of a phantom.

FIG. 2 shows a cross sectional view of the phantom 124 located where the slice 132 is. It can be seen that the phantom in this example 124 is circular and has two separate compartments 128, 130. This may be used to provide two separate sets of magnetic resonance signals for different or distinct materials. This may aid in more accurately determining the performance degradation conditions.

Figure 3:
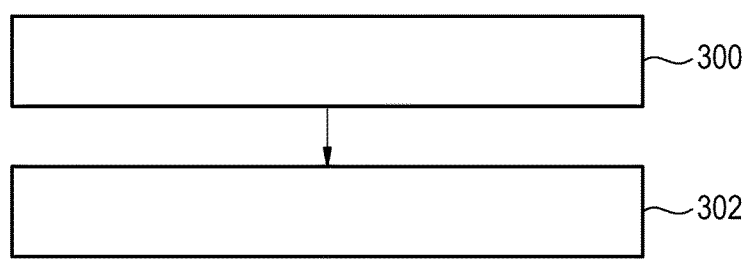
FIG. 3 shows a flow chart that illustrates a method of operating the magnetic resonance imaging system of FIG. 1.

FIG. 3 shows a flowchart which illustrates an example of a method of operating the magnetic resonance imaging system 100 of FIG. 1. First in step 300 the magnetic resonance data 152 is acquired by controlling the magnetic resonance imaging system 100 with the pulse sequence instructions 150. Next in step 302 the one or more performance degradation conditions 158 are determined by comparing the magnetic resonance data 152 with the magnetic resonance fingerprinting dictionary 154. This for instance may be done by including the data from the faults or potential off-spec behavior as a linear combination and matching this to the magnetic resonance data or by following an algorithm or a decision tree which systematically chooses the proper failure mode or state of the magnetic resonance fingerprinting dictionary.

MR Fingerprinting is a new and promising approach to obtain MR parameters or tissue specific information for potential classification. It is based on the idea to identify MR active species with certain MR related properties based on their MR response to a unique sequence of RF pulses, signal evolution periods which may include appropriate gradient switching schemes and etc. Based on a previously generated dictionary, that contains most of the possible MR responses conceivable or at least as many possible MR responses as is reasonable to include, pattern matching can be performed to identify the species.

This concept can however be applied in a reverse way, having one or a couple of known species (for example arranged in a phantom), which are fully described with respect to their MR properties, undergoing a specific fingerprinting-type MR sequence with the aim to characterize the overall MR system performance and integrity including the ability to also characterize the status of its individual components (like RF and gradient amplifiers, individual receivers, switches, patient bed etc.). This approach could potentially facilitate a better, more detailed and more importantly proactive system maintenance approach and can be called MR-system-fingerprinting.

A medical imaging device has to be frequently tested to prove diagnostic imaging quality to ensure clinical standards. Proactive or preventive maintenance is also an important aspect because appropriate concepts represent an aspect of potential cost reduction. Currently, on MRI systems installed at the customer sites, a periodic image quality test (PIQT) is performed which consists of a set of well-defined scans with well-defined, but different, classical MR sequences and contrasts to facilitate automatic evaluation based on post- and image-processing derived SNR measures, accessing roughly image quality, geometric accuracy and the like.

This PIQT is very helpful, but is actually asking only a limited amount of system related information and very specific questions, which may not reflect the entire status/performance/shape/future prospect of the system and its sub-components and do not necessarily indicate the source of potential image quality deviations. To get a better overview about the system performance and integrity, including also getting an idea which of the components are at risk to fail due to edgy or lacking performance, more sophisticated tests should be designed to improve system up-time at perfect image quality and to better predict future system/component failure which would enable to better plan service in advance and to further save resources. It is therefore desirable to design a better test which is also capable to quantitatively assess discrepancies in system performance, which would allow more specifically identifying and potentially correcting for system performance issues. While special test sequences can be designed that are sensitive to deviations of individual system parameters/components, more general test allowing all the different individual components of the MR system to interplay can lead to better sensitivity.

Examples disclosed herein may apply the new concept of MR fingerprinting in a reverse manner. Instead of deciphering the MR properties of a sample it is the idea to analyze the system properties including the subsystems, to help characterizing their status, their sensitivity to failure, or potential system/component malfunction already in advance preferable before actual system drop-out would take place helping to perform corrective maintenance and to identify potential components at risk.

For this purpose a dedicated sequence of mainly MR related pulses, MR system settings and events is generated (consisting out of elements like e.g.: RF pulses, gradient pulses, time delays, table positions, with changing MR sequence and also changing hardware parameters/settings like: gains, phases, frequencies, etc.) and applied to provoke in a MR-wise, well-defined, known and stable object (e.g. MR phantom) corresponding MR signal responses. Those responses are received mainly via the system's MR receivers and coils (which can also be part of the test), but also additional dedicated receiver/sensing sub-systems are conceivable (e.g. in case of a vast failure of the standard receiver chain). The measured MR signals can be analyzed with respect to known responses stored in an appropriate MR system response dictionary to find pattern correlation to identify actual or signs of future component malfunction.

A possible feature of this MR system analyzing approach, which can run like a PIQT over night without costing important scanning time, is in the dictionary. In contrast to the dictionaries used in MR fingerprinting, which are based on extensive Bloch-simulations including all kind of MR parameters and some insight in the way how an actual MR protocol is executed, in the present approach the dictionary is different. Here the tissue or phantom material specific MR parameters are known, given by the probe or the phantom to be used (at a given room temperature or another constant temperature), but all the potential deviations of the MR system components may be considered, incorporated and finally modelled. If this is done sufficiently it allows identifying specific component failure or component degradation based on the specific signature of the MR system response to a given predefined MR system fingerprinting sequence. Furthermore, quantitative information about the deviation of individual system parameters is obtained, which can be used for correction/system calibration purposes in the imaging scans and integrated in the MR fingerprinting dictionary (system-specific MRF dictionary) to improve the image quality/accuracy.

To predict the response of the entire MR device, not to the object under study in the first place, but to system/component imperfections their behavior has to be appropriately modelled. This is usually done via corresponding specifications with the deviations from the nominal values given. In this way different instances or states of the system and their components can be generated which influence the MR response to a certain input MR sequence challenge. Thus, for instance for an RF amplifier, different deviations from the linear behavior, different power losses, gain factor misssetting or etc. can be assumed. Those might reflect certain states of operation, aging phases, levels for being out of spec, malfunctions and so on which should be identified by their characteristic signature. The knowledge about these different states could be fed by knowledge available at the MR-field service, the manufacture of the components or from other sources like big data analysis about frequent failure features or degrading patterns.

Another possible element of examples is the definition of an appropriate MR sequence driving scheme that allows maximizing the diversity in the MR response for all the potential instances or states of the entire system which have to be addressed. Maximum diversity allows for a high specificity to identify the actual cause. To define an optimal MR sequence a guided search, some intuitive insight and also some brute force "trial and error" search in the "scanner state space" might be appropriate. A sequence containing segments (or sub-sequences) which are sensitive to individual system parameters as well as combinations of system parameters as well as noise measurements can be useful for comprehensive system characterization.

Example 1

A specially designed phantom, of known MR properties, placed on the patient table, with a surface coil array on top, connected to the parallel receive system of the MR scanner is used in this MR-system-fingerprinting approach. A dedicated sequence is applied to the system, the MR responses are recorded while the sequence is performed using the phased array and the corresponding receivers, digitized and stored for later analysis, e.g. via a pre-defined dictionary linking the MR response to the performance/status/integrity of system (sub-)components. In this special example no spatial resolution, means no imaging gradients are necessary. Therefore, in this example a very simple phantom can be used maybe a just a simple sphere filled with doped water of known MR properties.

In the present example, based on the measured data, properties of the individual sub-systems like the RF amplifier can be analyzed in detail regarding linearity, gain, reflection, etc.

Example 2

However a more complex phantom, like the one currently used for PIQT, could be useful. In another example spatial resolution is tested on top. This allows analyzing issues of spatial resolution, geometric accuracy and all the other aspects usually covered by the PIQT. For this purpose the MR-system-fingerprinting sequence has to be performed in a spatially resolved way and the dictionary based data evaluation may be performed pixel by pixel or in specific regions of interest. Subsequently, conventional testing routines similar to those of the PIQT can be applied additionally to the various maps and also to the simple core MR image.

A further refinement is not to test the entire system at once but use specific tests for sub-components. This would be helpful to reduce the complexity and the corresponding parameter space. Furthermore, this could help to rule out potential ambiguities if system imperfections in different sub-components appear similar in the MR-system-fingerprinting patterns if the "sequence" challenge was not appropriately chosen. Thus, a certain test for the proper behavior of sub-system can be performed first, followed by further ones. As an example, instead of testing the gradient and the higher order shim systems simultaneously together in a general setting, one could consider to run a corresponding system-fingerprinting test on all MR components excluding the normal gradients in the first run. In a second run the gradient system will be included after the higher order shims have been successfully system-fingerprinted already to function normally. This "selective" MR-system-fingerprinting procedure might also imply the use of dedicated response dictionaries and system probing MR sequences to more specifically probe the corresponding system state space.

The potential advantage of this new approach is that also rather complicated dependencies and interactions of individual system components can be modelled and identified which are difficult to sense with the existing way of "linear" system analysis. In the conventional scenario each individual component is tested, but in an independent, isolated way to keep the number of variables as small as possible. In this way, effects that results from slight underperformance of two or more parts of the MR system might not be detected, even if the consequences are reflected by an insufficient image quality.

A further possible refinement is that not only the core MR system but also e.g., the patient table or other peripheral components could be analyzed with respect to proper function.

In one example, the phantom contains one or several temperature sensors. These sensors may serve two purposes: First, a temperature measurement before the scan can provide helpful information to improve the accuracy of the calculation of expected measurement signals. Second, measurement of temperature variations during the fingerprint scan can, monitoring power deposition, can be made part of the fingerprint itself.

In a further example, a (simple) test transmitter and/or receiver could be added to the MR system for service purposes using the proposed MR-system-fingerprinting. This test device would allow performing the proposed service functions in case that a system failure results in insufficient signal from the standard RF chain. Low signal levels could otherwise impede the specific interpretation of system components by a dictionary.

Figure 4:
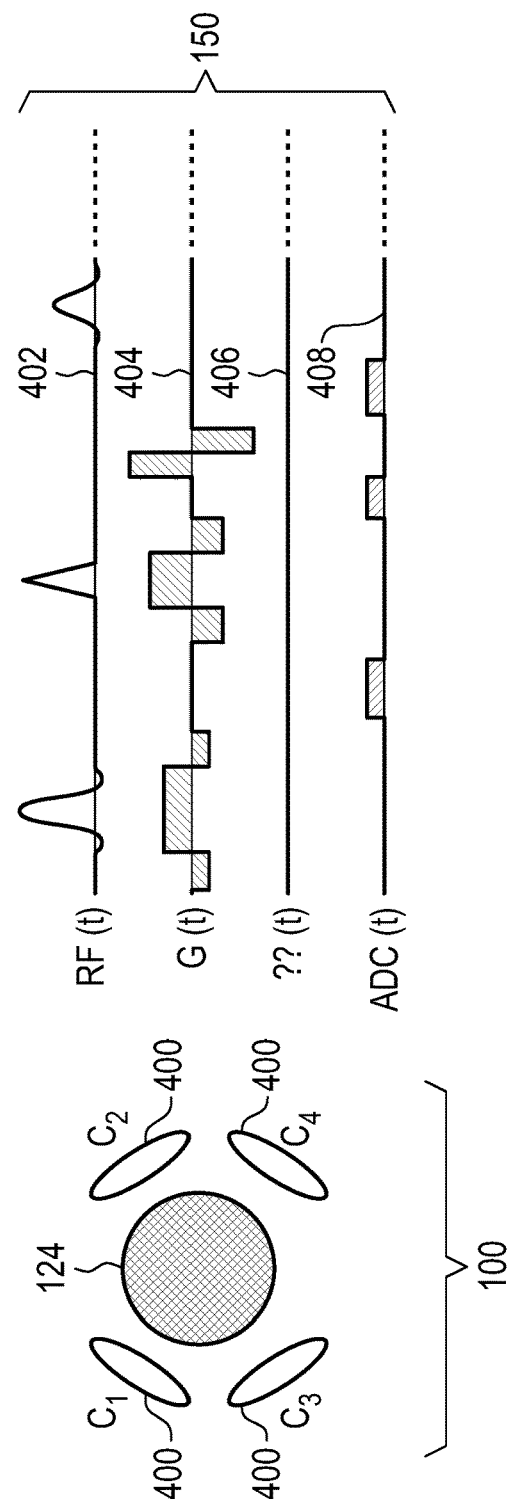
FIG. 4 illustrates a magnetic resonance imaging system and a pulse sequence.

FIG. 4 shows an example of a magnetic resonance setup 100 and a pulse sequence 150. The magnetic resonance setup 100 has a phantom 124 and a number of receive coils 400 that are labeled C1-C4. The pulse sequence 150 shows several features. There is an indication of when pulse sequences 402 are used to excite spins within the phantom 124. A number of different gradient pulses indicated by the line 404 may also be used. The line 406 indicates space where various parameters of the magnetic resonance system may be varied. Depending upon the tests that are performed different system parameters 406 may be varied. The line 408 indicates when measurements are performed.

As explained above, FIG. 4 shows an example of an MR set-up/sequence used for MR-system-fingerprinting: 100 Phantom and individual receive coils (C1-C4) to receive an MR signal. 150 A number of RF or gradient pulses 402 are used to create MR signal in a known phantom. During this measurement different system component parameters (also indicated by the trace denoted with "??" in 150) are varied while the MR signal of the known object is sampled using the receive system of the of the MR scanner.

Figure 5:
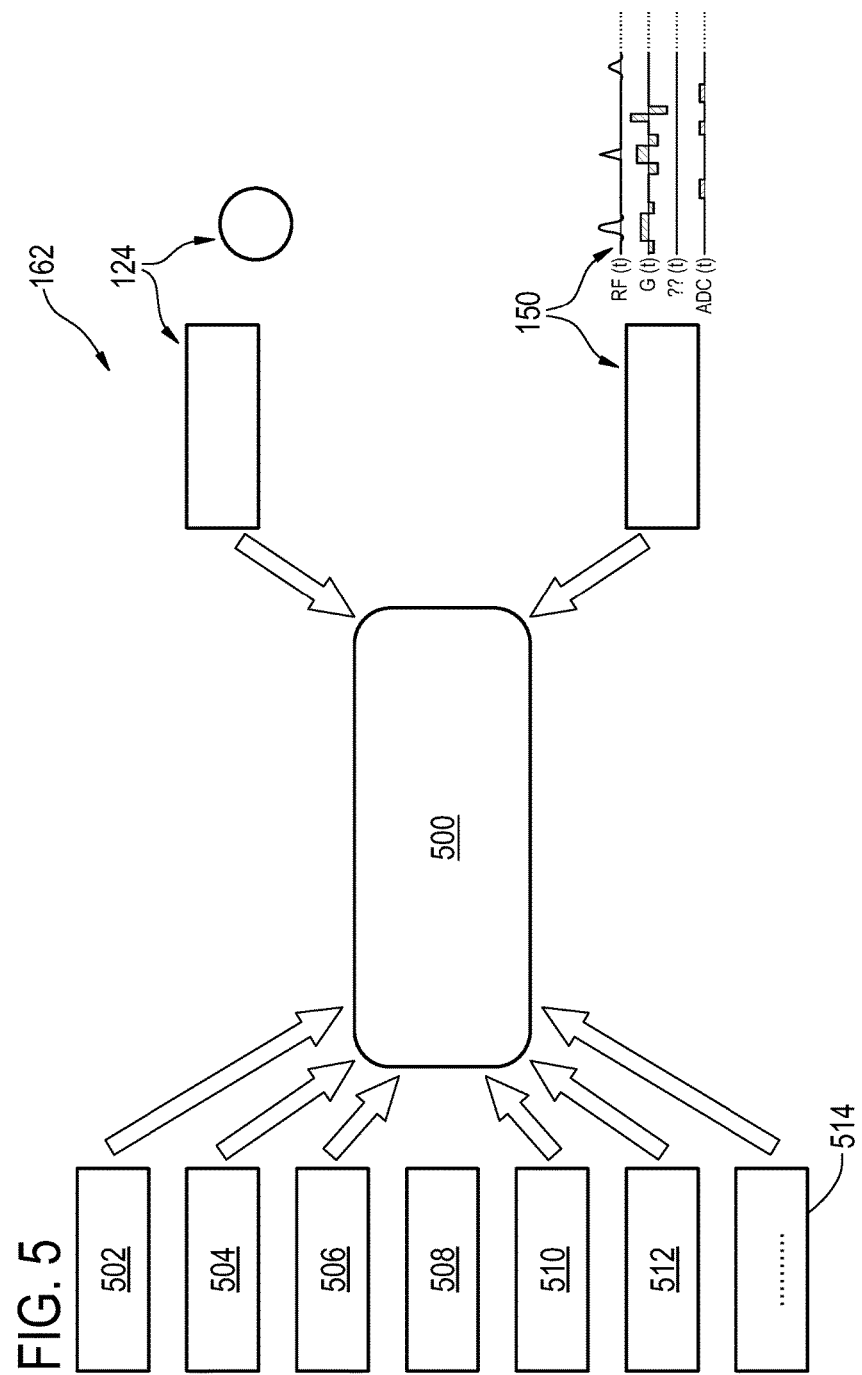
FIG. 5 illustrates the generation of a magnetic resonance fingerprinting dictionary.

FIG. 5 illustrates a module 162 or a method for the generation of the magnetic resonance system fingerprinting dictionary 500. The block 500 corresponds to the constructed dictionary and also the code for performing the block simulation. The block system may be performed for a particular spin system 124 and a particular magnetic resonance sequence 150. For this known spin system 124 and the known magnetic resonance system 150 various other parameters may be varied to provide the dictionary. For instance there may be variations in the radio-frequency system 502, the gradient system 504, the receive system 506, the magnet system 508, the patient table 510, the physiology system 512 or other system parameters 514 may also be varied.

FIG. 5 shows an example for the generation of a MR-system-fingerprinting dictionary. All different MR system components including their different states and parameters (specific properties) form a multi-dimensional space which might affect the outcome of an MR experiment using a known object and a given MR sequence (a succession of different MR related events). All these different source of influence are simulated to form the dictionary which reflects potential responses of the entire system including the phantom to the MR sequence.

Figure 6:
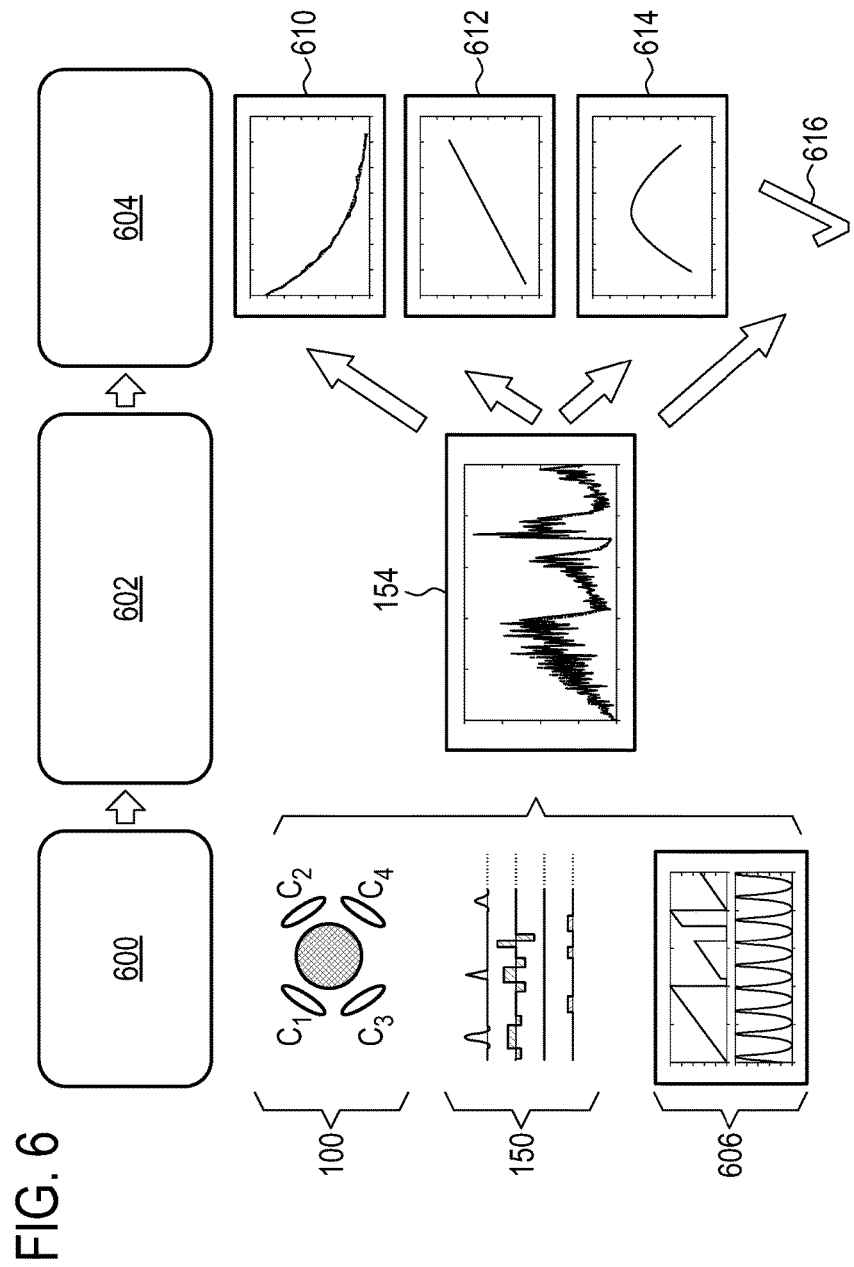
FIG. 6 illustrates a method of performing magnetic resonance system fingerprinting.

FIG. 6 illustrates a general scheme for forming magnetic resonance system fingerprinting. This is divided into three parts. The first part 600 corresponds to the experimental or acquisition of data. Part 2 corresponds to pattern recognition or dictionary mapping 602. Part 3 corresponds to system and component characterizations 604. The first step, the experimental acquisition of the magnetic resonance data comprises the physical system 100, the pulse sequence 150 and the variation of various magnetic resonance parameter sets 606. In step 602 the results or the acquired magnetic resonance data is then compared to the magnetic resonance fingerprinting dictionary 154. In step 604 the system is characterized for example using a variety of system transfer functions 610, 612, 614. If no faults are identified this may also correspond to a final system acceptance criteria 616.

FIG. 6 shows a general scheme of an MR-system-fingerprinting approach. Using (100) the phantom and (150) the appropriate MR-system-fingerprinting MR sequence employing (606) useful MR parameters sets (here flip angle and TR are shown for illustration) the resulting signal answer is analyzed in (154) via the previously generated dictionary. The pattern recognition maps the measured data to corresponding system transfer functions 610, 612, 614 or subsets of that helping to characterize the entire MRI system and also sub-components resulting into a final system acceptance criteria 616.

Figure 7:
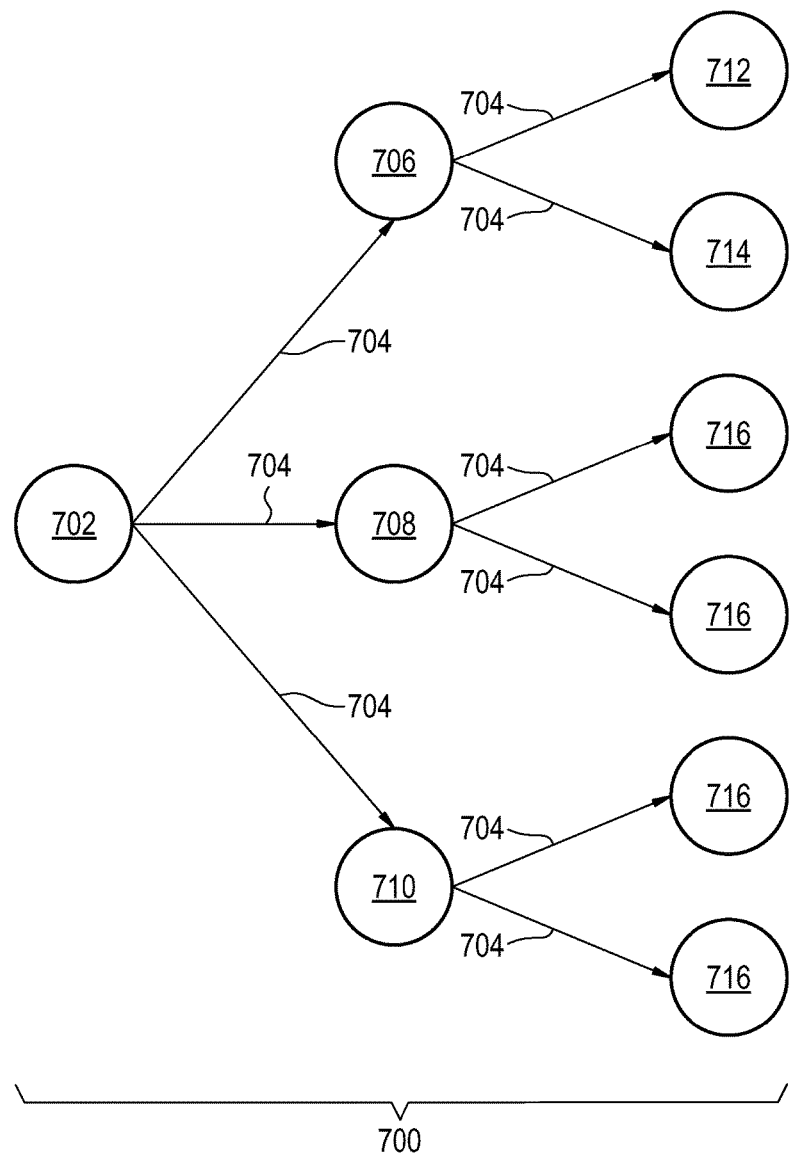
FIG. 7 illustrates a decision tree.

FIG. 7 illustrates an example of a decision tree 700. The decision tree may be used to structure the magnetic resonance fingerprinting dictionary and the pulse sequence instructions. For example the decision tree may comprise a first entry 702. The first entry may comprise a portion of the magnetic resonance fingerprinting dictionary and pulse sequence instructions. The portion of the pulse sequence instructions that correspond to the first node 702 are executed and then these are compared to the magnetic resonance fingerprinting dictionary. Next the results of the comparison may decide in the selection of one of the three branches 704. The branches are shown as pointing to a third entry 706, of fourth entry 708, and a fifth entry 710. For example the comparison to the magnetic resonance fingerprinting dictionary may lead to the method following to the third entry 706. When the third entry is reached 706 a further portion of the pulse sequence instructions are executed and then compared to another portion or section of the magnetic resonance fingerprinting dictionary. This may then lead to the branches 704 which point to nodes 712 and 714. Node 712 corresponds to a first performance degradation condition and node 714 corresponds to a second performance degradation condition. From the nodes 708 and 710 may lead to additional or subsequent 716 performance degradation conditions. By following a path through the decision tree 700 of faults, errors, or degradation conditions in the magnetic resonance system may be accurately and quickly identified.

The measured MR signal may be compared with the magnetic resonance fingerprinting dictionary. The dictionary is created by solving the Bloch equations for the fingerprinting sequence with variations in the performance of components of the magnetic resonance system.

In some examples faults in the individual system components/modules are decoupled from each other. In other examples this is not the case, for example if a certain component (e.g. the RF transmit amplifier) is broken then no MR signal can be obtained at all, but even this simple situation is not unique, means if we do not measure an MR signal a plenty of other reasons could be responsible (an RF amplifier fault is just one among other options).

A slight degrading of the RF amplifier could be sensed as a degrading/mismatch/disoperation of many other MR system components. This underlines that not all individual system components are decoupled. Imagine that the linearity look-up table of the RF amplifier is not properly updated or is outdated due to many reasons (e.g. component aging in the RF amp, etc.). This could manifest itself as a change in SNR, which for instance could result from a fault in the receive system, a not proper working receive pre-amplifier, a lost isolation/shielding from some power supply which might all of a sudden generate frequency components near the Lamar frequency, a leaking Faraday cage (an open door), and lots of other issues which can be uniquely be identifies in the first place. Furthermore, if a certain sub-system is working on the edge it might influence other sub-subsystem in a linear and also non-linear manner—in short there is also a sub-system coupling.

Therefore, and also to reduce the complexity a multi-layer system analysis could be envisioned. Starting form a certain level of complexity, multiple and different MR-system-fingerprinting sequences can be applied to test multiple system components simultaneously and in their synergy/joint action. This might be beneficial, because in some cases individual, isolated components could function fine, but problems arise just when they have to work together. Based on the outcome and the evaluation results of such individual tests an appropriate decision tree is used, driven by lots of prior knowledge (most probable system failures, relationships to other components, etc.) to issue additional and partially very specific fingerprinting test/sequences which are prescribed to specifically probe system features.

A further aspect is that the system response changes as a function of time (over weeks, month), this can also show very specific feature which could be understood as a fingerprint of a degrading component so that also the response tracking over time (much bigger than the actual fingerprinting sequence could be useful.

Different components of the magnetic resonance system may manifest failures in different ways.

System Degradation in the RF System:
   In case of an aging RF amplifier the RF tube specific parameters may alter (linearity, maximum power, etc.) in a characteristic way changing the RF output. Those changes can be captured via fingerprinting. The RF output stability can change especially during the warm up and during the initial phase of RF amplifier operation, can be sensed and correlated with corresponding aging/malfunction probabilities.
   Components in the RF transmit body coil could also fail or alter over time. Arcing in the body or specific voltage drops can result into serious non-linearity effects. Arcs can give rise to serious spikes in the MR measured signal which can be identified in the data. Spikes are very common events which can have also many other reasons or interaction causes (gradient switching, mechanical resonances etc.)

System Degradation in the Gradient System:
   Faults of the gradient amplifier are often easily identified by very special system component tests, (but aging of the gradient coils?).
   Mechanical issues are present, gradient switching include high mechanical forces resulting that parts might get loose and start to oscillate. This change in wiring can change the acoustic sound of the coil but furthermore the eddy current behavior and potentially also the performance and linearity which can be picked up by Fingerprinting.
   Arcing could take place if high slew rate are used in the fingerprinting sequence which might result in spikes . . . .

System Degradation in the Receive System:
   Ageing components can result in changes of the receive coil behavior like: Increased noise figure or total drop out, frequency de-tuning, increased coupling of neighboring coil elements The test phantom can be constructed in different ways. The phantom preferably yields a reproducible MR signal. It preferably consists of one or several well-known substance(s) which are encapsulated in a tight container so that their properties do not change over time. The phantom could also include a temperature stabilization system, possibly consisting of a heating element, one or several temperature sensors, an inner enclosure made of a material with high thermal conductance and heat capacity (but preferably no metal), e.g. a ceramic material and an outer enclosure made of a thermally insulating material. The phantom may also be placed at a well-known position in the MR scanner. This could be achieved by incorporating mounting holes or clamps in the patient table, where the phantom is placed in a reproducible way.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance system
104 magnet
106 bore of magnet
108 measurement zone or imaging zone
110 magnetic field gradient coils
112 magnetic field gradient coil power supply
114 radio-frequency coil
116 transceiver
118 subject
120 subject support
122 actuator
124 phantom
126 phantom mount
128 first compartment
130 second compartment
132 slice
136 computer system
138 hardware interface
140 processor
142 user interface
144 computer storage
146 computer memory
150 pulse sequence instructions
152 magnetic resonance data
154 magnetic resonance fingerprinting dictionary
156 magnetic resonance image
158 identified performance degradation conditions
160 control module
162 magnetic resonance fingerprint dictionary generating module
164 image reconstruction module
166 repair database
300 acquire the magnetic resonance data by controlling the magnetic resonance system with pulse sequence instructions
302 determine one or more performance degradation conditions of the magnetic resonance system by comparing the magnetic resonance data with a magnetic resonance fingerprinting dictionary
400 receive coils
402 RF pulses
404 gradient pulses
408 arbitrary system parameters
410 measurement times
500 dictionary and Bloch simulation
502 RF system
504 gradient system
506 receive system
508 magnet system
510 patient table
512 physiology system
514 other systems
516 spin system (phantom)
518 MR sequence
600 experimental MR-system-fingerprinting
602 pattern recognition or dictionary mapping
604 system and component characterization
606 MR parameter sets
610 system transfer function
612 system transfer function
614 system transfer function
616 final system acceptance criteria
700 decision tree
702 first entry
704 branch
706 third entry
708 fourth entry
710 fifth entry
712 first performance degradation condition
714 second performance degradation condition
716 subsequent performance degradation condition

The invention claimed is:

1. A method of operating a magnetic resonance system for acquiring magnetic resonance data from a phantom within a measurement zone, wherein the phantom comprises a known volume of at least one predetermined substance, wherein the method comprises the steps of:
acquiring the magnetic resonance data by controlling the magnetic resonance system with pulse sequence instructions, wherein the pulse sequence instructions cause the magnetic resonance system to acquire the magnetic resonance data according to a magnetic resonance fingerprinting technique, wherein the pulse sequence instructions specify a train of pulse sequence repetitions, wherein each pulse sequence repetition has a repetition time chosen from a distribution of repetition times, wherein each pulse sequence repetition comprises a radio frequency pulse chosen from a distribution of radio frequency pulses, wherein the distribution of radio frequency pulses cause magnetic spins to rotate to a distribution of flip angles, and wherein each pulse sequence repetition comprises a sampling event where the magnetic resonance signal is sampled for a predetermined duration at a sampling time before the end of the pulse sequence repetition, wherein the sampling time is chosen from a distribution of sampling times, wherein the magnetic resonance data is acquired during the sampling event; and
determining an occurrence of one or more performance degradation conditions, faults or malfunctions of the magnetic resonance system by comparing the magnetic resonance data with a magnetic resonance fingerprinting dictionary, wherein the magnetic resonance fingerprinting dictionary contains a listing of magnetic resonance signals for a set of system states in response to execution of the pulse sequence instructions for each of the at least one predetermined substance, wherein the set of system states represent faults, malfunctions, and/or performance degradations conditions by different components of the magnetic resonance system.

2. The method of claim 1, wherein the pulse sequence instructions comprises multiple segments, wherein the magnetic resonance fingerprinting dictionary is arranged as a decision tree for determining the one or more faults that comprises each of the multiple segments, wherein the decision tree has multiple entries, wherein each of the multiple entries connected by branches, wherein the multiple segments of the pulse sequence instructions comprises a first segment, wherein the multiple entries of the decision tree comprise a first entry which corresponds to the first segment, wherein the method further comprises:

controlling the magnetic resonance system with the first segment to acquire a first portion of the magnetic resonance data;

comparing the first portion of the magnetic resonance data to the first entry in the decision tree to choose a branch which identifies a subsequent segment of the pulse sequence data; and traversing the decision tree to identify the one or more faults by repeatedly controlling the magnetic resonance system with the subsequence segment and re-identifying the subsequence segment using the branches of the decision tree.

3. The method of claim 1, wherein the one or more faults is two or more faults, wherein the two or more faults are identified as a linear combination of the set of system states.

4. The method of claim 1, wherein the magnetic resonance system is a magnetic resonance imaging system, wherein the measurement zone is an imaging zone, wherein the magnetic resonance system further comprises:

a magnet for generating a main magnetic field within the measurement zone;

a magnetic field gradient system for generating a gradient magnetic field within the measurement zone to spatially encode the magnetic resonance data; and wherein the pulse sequence instructions further comprises instructions to control the magnetic field gradient system to perform spatial encoding of the magnetic resonance data during acquisition of the magnetic resonance data, wherein the spatial encoding divides the magnetic resonance data into discrete voxels.

5. The method of claim 4, wherein execution of the machine executable instructions further causes the processor to calculate the magnetic resonance fingerprinting dictionary by modeling each of the predetermined substances as one or more spins with the Bloch equations for each of the discrete voxels and for each of the set of system states.

6. The method of claim 4, wherein the at least one predetermined substances is two or more substances, wherein the phantom comprises a separate compartment for each of the two or more substances and for different combinations of the set of system states.

7. The method of claim 1, wherein the magnetic resonance system is an NMR spectrometer, wherein execution of the machine executable instructions further causes the processor to calculate the magnetic resonance fingerprinting dictionary by modeling each of the predetermined substances with the Bloch equations for each of the discrete voxels and for each of the set of system states.

8. The method of claim 1, wherein the phantom comprises a temperature control system, wherein the method further comprises maintaining the phantom temperature within a predetermined temperature range during the acquisition of the magnetic resonance data.

9. The method of claim 1, wherein the magnetic resonance system comprises a phantom mount for mounting the phantom in a predefined location in the measurement zone, wherein the method further comprises placing the phantom into the phantom mount before acquiring the magnetic resonance data.

10. The method of claim 1, wherein each pulse sequence repetition comprises at least one gradient pulse chosen from a distribution of gradient pulses.

11. The method of claim 1, wherein the method further comprises providing maintenance instructions by comparing the one or more performance degradation conditions to a repair database.

12. The method of claim 11, wherein the method further comprises performing the maintenance instructions to repair the magnetic resonance system.

13. A magnetic resonance system for acquiring magnetic resonance data from a phantom within a measurement zone, wherein the phantom comprises a known volume of at least one predetermined substance, wherein the magnetic resonance system comprises:

a memory for storing pulse sequence instructions and machine executable instructions, wherein the pulse sequence instructions cause the magnetic resonance system to acquire the magnetic resonance data according to a magnetic resonance fingerprinting technique, wherein the pulse sequence instructions specify a train of pulse sequence repetitions, wherein each pulse sequence repetition has a repetition time chosen from a distribution of repetition times, wherein each pulse sequence repetition comprises a radio frequency pulse chosen from a distribution of radio frequency pulses, wherein the distribution of radio frequency pulses cause magnetic spins to rotate to a distribution of flip angles, and wherein each pulse sequence repetition comprises a sampling event where the magnetic resonance signal is sampled for a predetermined duration at a sampling time before the end of the pulse sequence repetition, wherein the sampling time is chosen from a distribution of sampling times, wherein the magnetic resonance data is acquired during the sampling event;

a processor for controlling the magnetic resonance system: wherein execution of the machine executable instructions cause the processor to:

acquire the magnetic resonance data by controlling the magnetic resonance system with pulse sequence instructions; and determine occurrence of one or more performance degradation conditions, faults or malfunctions of the magnetic resonance system by comparing the magnetic resonance data with a magnetic resonance fingerprinting dictionary, wherein the magnetic resonance fingerprinting dictionary contains a listing of magnetic resonance signals for a set of system states in response to execution of the pulse sequence instructions for each of the at least one predetermined substance, wherein the set of system states represent faults, malfunctions, and/or performance degradations conditions by different components of the magnetic resonance system.

14. A computer program product comprising machine executable instructions stored on a non-transitory computer readable medium for execution by a processor controlling a magnetic resonance system for acquiring magnetic resonance data from a phantom within a measurement zone, wherein the phantom comprises a known volume of at least one predetermined substance, wherein the magnetic resonance system comprises a memory for storing pulse sequence instructions, wherein the pulse sequence instructions cause the magnetic resonance system to acquire the magnetic resonance data according to a magnetic resonance fingerprinting technique, wherein the pulse sequence instructions specify a train of pulse sequence repetitions, wherein each pulse sequence repetition has a repetition time chosen from a distribution of repetition times, wherein each pulse sequence repetition comprises a radio frequency pulse chosen from a distribution of radio frequency pulses, wherein the distribution of radio frequency pulses cause magnetic spins to rotate to a distribution of flip angles, and wherein each pulse sequence repetition comprises a sampling event where the magnetic resonance signal is sampled for a predetermined duration at a sampling time before the end of the pulse sequence repetition, wherein the sampling time is chosen from a distribution of sampling times, wherein the magnetic resonance data is acquired during the sampling event; wherein execution of the machine executable instructions cause the processor to:

acquire the magnetic resonance data by controlling the magnetic resonance system with pulse sequence instructions; and determine occurrence of one or more performance degradation conditions, faults or of the magnetic resonance system by comparing the magnetic resonance data with a magnetic resonance fingerprinting dictionary, wherein the magnetic resonance fingerprinting dictionary contains a listing of magnetic resonance signals for a set of system states in response to execution of the pulse sequence instructions for each of the at least one predetermined substance, wherein the set of system states represent faults, malfunctions, or performance degradations conditions by different components of the magnetic resonance system.

* * * * *